(12) United States Patent
Marttila

(10) Patent No.: US 6,646,733 B1
(45) Date of Patent: Nov. 11, 2003

(54) METHOD FOR INSPECTING ELECTRODE SURFACE QUALITY

(75) Inventor: Tom Marttila, Espoo (FI)

(73) Assignee: Outokumou Oyj, Espoo (FI)

( * ) Notice: Subject to any disclaimer, the term of this patent is extended or adjusted under 35 U.S.C. 154(b) by 0 days.

(21) Appl. No.: 10/129,869

(22) PCT Filed: Oct. 27, 2000

(86) PCT No.: PCT/FI00/00932

§ 371 (c)(1),
(2), (4) Date: May 9, 2002

(87) PCT Pub. No.: WO01/35083

PCT Pub. Date: May 17, 2001

(30) Foreign Application Priority Data

Nov. 9, 1999 (FI) ............................................. 19992406

(51) Int. Cl.[7] .............................................. G01N 21/00
(52) U.S. Cl. .................................... 356/237.1; 250/311
(58) Field of Search ......................... 356/237.1–237.6, 356/601, 614; 250/311, 559.07, 559.08, 559.19, 559.2, 559.22, 559.23, 559.34, 374, 385.1, 225; 204/1 T, 192.32, 192.34, 192.38, 298.41

(56) References Cited

U.S. PATENT DOCUMENTS

| 4,498,960 | A | * | 2/1985 | Rubinstein ................. 204/1 T |
| 4,919,766 | A | | 4/1990 | Kotowski et al. |
| 5,440,391 | A | | 8/1995 | Smeyers et al. |
| 5,451,308 | A | * | 9/1995 | Sablev et al. .......... 204/298.41 |
| 5,614,722 | A | * | 3/1997 | Solberg et al. ............. 250/374 |
| 5,767,516 | A | * | 6/1998 | Kawanami et al. ......... 250/311 |
| 5,774,224 | A | | 6/1998 | Kerstens |
| 5,951,372 | A | * | 9/1999 | Choquette et al. ..... 204/192.23 |
| 5,986,763 | A | * | 11/1999 | Inoue ......................... 356/601 |
| 6,038,018 | A | * | 3/2000 | Yamazaki et al. ....... 356/237.1 |
| 6,194,705 | B1 | * | 2/2001 | Nakada et al. .............. 250/225 |
| 6,437,355 | B1 | * | 8/2002 | Nishino ................. 250/559.19 |

FOREIGN PATENT DOCUMENTS

| DE | 3431148 A1 | 3/1986 |
| JP | 11-148807 | 6/1999 |

* cited by examiner

Primary Examiner—Frank G. Font
Assistant Examiner—Sang H. Nguyen
(74) Attorney, Agent, or Firm—Morgan & Finnegan, LLP

(57) ABSTRACT

The invention relates to a method for inspecting the surface quality of the deposit created on the surface of an electrode in the electrolytic treatment of metals. According to the invention, a cathode (1) obtained from electrolytic treatment is illuminated by at least one light source (3) placed in an oblique position with respect to the plane (12) that constitutes the cathode surface, and an image of the illuminated surface (12) is made with at least one camera (8); said image is then transmitted to an image processing arrangement (9), and on the basis of said image, there are defined possible irregularities of the surface in order to classify the deposit (11) located on the cathode for the next processing step.

15 Claims, 2 Drawing Sheets

METHOD FOR INSPECTING ELECTRODE SURFACE QUALITY

FIELD OF THE INVENTION

The present invention relates to a method for inspecting the surface quality of the deposit created on the surface of an electrode in the electrolytic treatment of metals by means of an image made of the electrode surface.

BACKGROUND OF THE INVENTION

In the electrolytic treatment of metals, the desired metal is precipitated on the surface of the electrode, i.e. cathode, used in the electrolytic treatment. The treatment is performed by means of electric current in a tank designed for electrolytic treatment; in said tank, there is provided liquid, i.e. electrolyte, and in said electrolyte there is partially immersed a number of plate-like anodes and plate-like cathodes in an alternating fashion and made electro conductive material. The desired metal is precipitated onto the cathode either so that in the electrolytic treatment, there is used a soluble anode made of the same metal as the one to be precipitated, like in the precipitation of copper, or so that in the electrolytic treatment, there is used an insoluble anode, like in the precipitation of zinc or nickel, and that the metal to be precipitated is dissolved in the electrolyte used in the electrolytic treatment and is precipitated directly from the electrolyte onto the cathode.

In connection with the precipitation process carried out in the electrolytic treatment of metals, the electrolyte usually contains small amounts of impurities that are obtained either from the electrolyte itself or from the metal to be precipitated; said impurities tend to be precipitated onto the cathode along with the rest of the deposit. Moreover, the electrolyte may contain gas bubbles that affect the formation of the deposit. Moreover, the electric current density in the electrolytic treatment may fluctuate, in which case the precipitation of metal onto the cathode varies at different spots of the cathode surface. Impurities, gas bubbles and fluctuations in the current density cause irregularities, i.e. nodules, on the cathode surface, and said nodules affect the classification of the cathode for further treatment. The detection of nodules on the cathode surface by visual inspection is difficult and slow, particularly as there are hundreds of cathodes being processed daily in the production plants of the current scale.

SUMMARY OF THE INVENTION

The object of the present invention is to eliminate drawbacks of the prior art and to achieve a method for inspecting the electrode surface quality on the basis of an image made of the electrode surface. The essential novel features of the invention are apparent from the appended claims.

According to the invention, in a tank designed for electrolytic treatment, there is provided liquid, i.e. electrolyte, for conducting the electric current; in said liquid, there are at least partly immersed plate-like anodes and cathodes made of an electro conductive material and arranged in an alternating fashion, in order to precipitate the desired metal onto electrode serving as the cathode. In the end of the precipitation process, the cathode complete with the deposit is lifted out of the tank, whereafter the cathode is subjected to an inspection process according to the invention in order to classify said cathode on the basis of the cathode surface quality. The cathode surface quality inspection according to the invention is advantageously carried out prior to stripping the deposit from the cathode mother plate, in connection with the transportation from the electrolytic tank to the stripping station. In order to inspect the cathode surface quality, in the immediate vicinity of the cathode conveyor track, there is provided at least one checkpoint where the cathode surface is illuminated with at least one light source from a direction that is oblique with respect to the cathode conveyor track, in which case the irregularities of the cathode surface cast shadows on said surface. In the checkpoint, there also is installed at least one camera that makes an image from the illuminated cathode surface or monitors the illuminated surface in an essentially continuous fashion. The image obtained of the cathode surface is further transmitted to an image processing device where the image is processed by measuring physical qualities of the shadows cast by the irregularities. On the basis of the physical qualities of the shadows, the cathode is classified in a desired fashion.

In a preferred embodiment of the invention, the inspection of the quality of a cathode surface is carried out while conveying cathodes in a transversal conveyor that is connected to the operation of a cyclically operated stripping station and is thus itself cyclically operated. In a cyclically operated transversal conveyor, the cathode movement is stopped during the stripping of the deposit that takes place in the stripping station. Thus the inspection according to the invention is advantageously carried out in one inspection station for one cathode at a time. When necessary, the cathode can also be inspected in several inspection stations.

For the cathode surface quality inspection according to the invention, in the inspection station there is installed at least one light source, so that the beams generated by the light source are directed to the surface of the cathode to be inspected at an oblique angle, the size of said angle varying within the range 0–90 degrees, advantageously 30–60 degrees. Now the possible irregularities of the surface cast shadows on the cathode surface, and the length and area of said shadows are directly proportional to the length and area of the irregularity in question. In order to define the surface quality of the illuminated cathode, the inspection station also includes at least one camera that is advantageously installed in an essentially perpendicular position with respect to the cathode surface under inspection; by means of said camera, there is obtained an image of the illuminated surface that may include shadows caused by possible irregularities. When desired, the camera can also be installed in a spot and at an angle that deviate from the essentially perpendicular position in relation to the surface of the cathode under inspection, but so that the shadows caused by irregularities on the cathode plate surface can still be an object for making an image. The image is transmitted from the inspection station to an image processing device, where the length and area of the shadows contained in the image are measured, and for instance the number and location of the shadows is defined. On the basis of the results obtained in the inspection, the deposits to be stripped from the cathode mother plate in the stripping station are classified in various classes for further processing.

In the cathode surface inspection according to the invention, there is advantageously used one light source for each surface to be illuminated. Thus the shadows cast by possible irregularities are made essentially sharp-edged and hence essentially easily definable, because the light causing the shadow comes from one direction only, and beams coming from several different light sources do not intersect. It is, however, possible that in the inspection according to the invention there are used at least two light sources for each illuminated surface, but this type of arrangement is advantageous essentially in cases where the irregularities as such are sharp-edged.

A light source meant for the illumination of the surface to be inspected is installed, with respect to the surface to be illuminated, so that the light source is located outside the area that is formed by the normals of the plane that constitutes the cathode surface. Thus the light source is placed at an oblique angle with respect to the normal of the plane that constitutes the surface to be illuminated, and the size of said angle is within the range 0–90 degrees, advantageously 30–60 degrees when measured at the spot where the beams coming from the light source meet the central line of the plane defined to be in the inspection station. In position and location, said plane defined to be in the inspection station essentially corresponds to the plane formed by the cathode to be illuminated. By adjusting the angle of the light source with respect to the normal of the plane that constitutes the surface to be illuminated towards a sharper angle, the length of the shadows cast by possible irregularities can be extended, in which case the dimensions of the irregularities can be defined in and advantageously more accurate fashion. The employed light source can be for instance a halogen floodlight, a fluorescent tube or an incandescent lamp. When necessary, in front of the light source, there can be arranged radiant field stops that guide the proceeding of the beams onto the surface to be illuminated.

In the method according to the invention, the image of the illuminated cathode surface is advantageously shot by one camera per each surface to be illuminated. When desired, the number of said cameras can be two or more, in which case the dimensions of the shadows cast by possible irregularities can be defined as the average of two or more images. When using two or more cameras, the positioning of said cameras can be used to particularly affect possible special dimensions to be defined on the basis of the obtained image, which special dimensions should be defined in connection with the inspection. While using two or more cameras, the cameras can be chosen so that they represent different types, in which case for instance one camera is a video camera, and the other is a photographic camera. On the other hand the angle where the beams coming from the light sources meet the central point of the plane that constitutes the cathode surface is maintained the same.

The camera that shoots a picture of the illuminated cathode surface is installed, with respect to the surface of the cathode to be inspected, so that the camera is located in an essentially perpendicular position with respect to the plane that constitutes the cathode surface. The camera is installed so that the image obtained in the camera is sharp at least in one spot of the cathode surface. Advantageously the camera is installed so that it is located in an essentially central position in the area where the cathode under inspection is stopped by the conveying operation for performing the inspection. When using two or more cameras, the cameras are positioned, mutually and with respect to the plane to be monitored, advantageously in an essentially symmetrical fashion.

In the method according to the invention, the image made of the cathode surface under inspection is further transmitted to an image processing device; in said device, there is installed a computer program that calculates for instance the number, size and primary location of shadows and thus the number, size and primary location of corresponding irregularities contained on the cathode surface. The measurement results are recorded in a microprocessor included in the image processing device, and the obtained results are used for classifying the deposit located on the cathode. By means of the calculated values and the recorded history, the deposit to be stripped from the cathode is classified according to the further processing steps that are most reasonable for the deposit in question. On the basis of the recorded history information, possible changes in the electrolytic process can also be detected, because for instance changes in the location of irregularities are usually caused by changes in the conditions of the electrolytic process itself.

BRIEF DESCRIPTION OF THE DRAWINGS

The invention is explained in more detail with reference to the appended drawings, where.

DETAILED DESCRIPTION OF THE INVENTION

Figure 1:
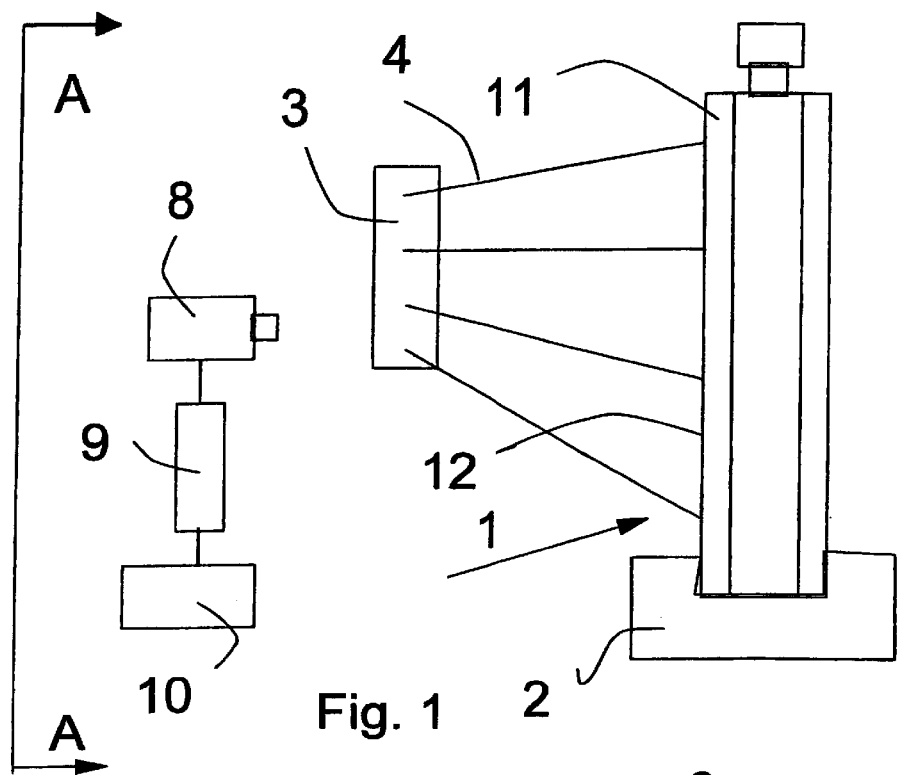
FIG. 1 represents a preferred embodiment of the invention when seen as a schematical illustration from behind the camera used in said embodiment.
Figure 2:
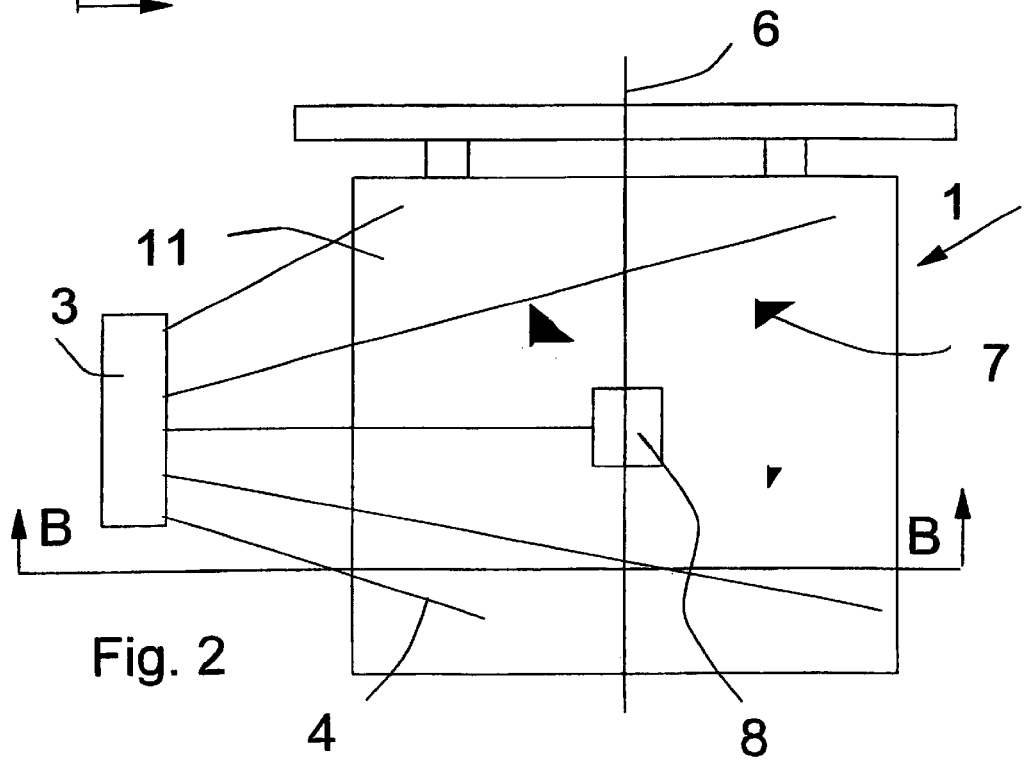
FIG. 2 illustrates a preferred embodiment according to FIG. 1, when seen in the direction A—A.
Figure 3:
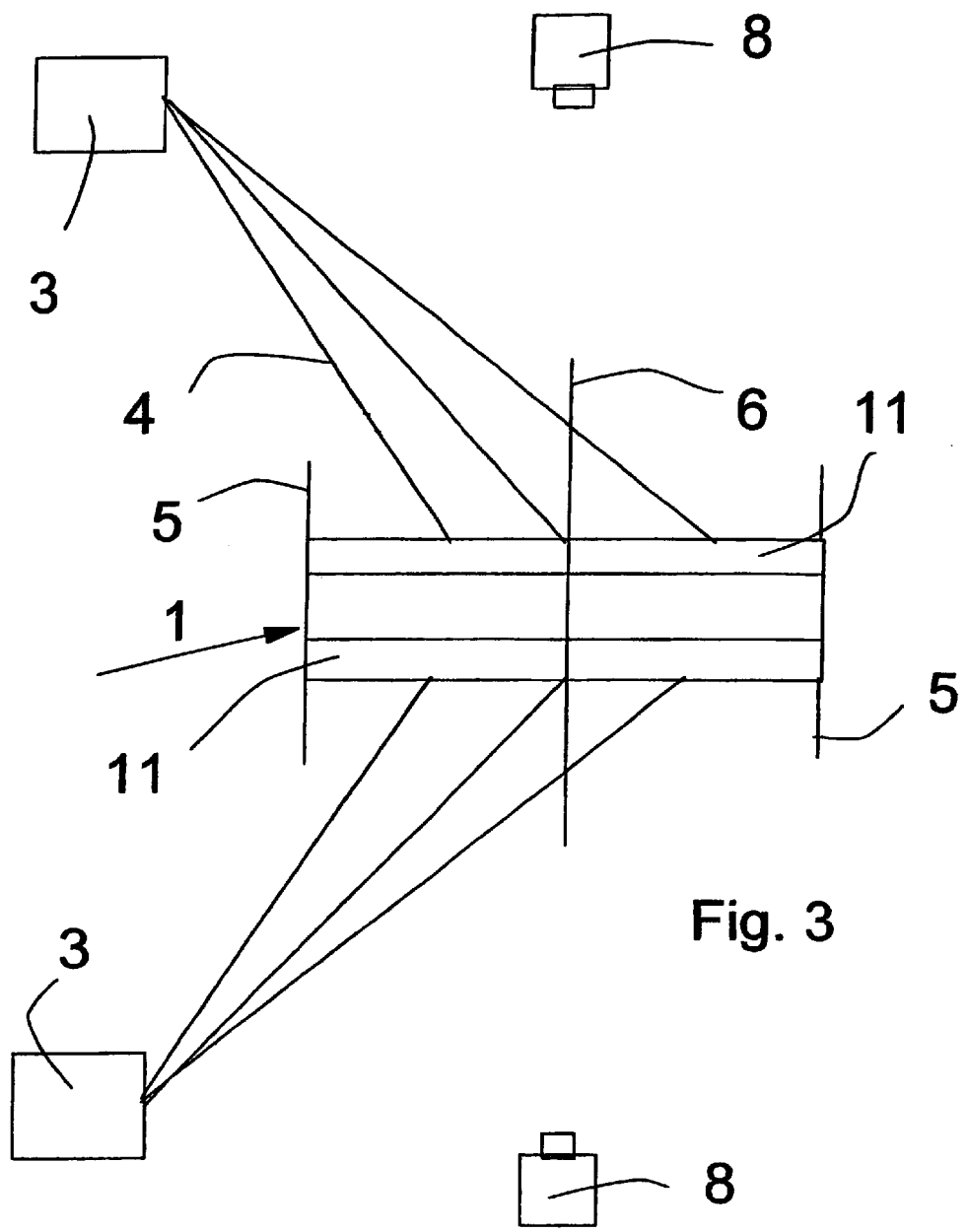
FIG. 3 illustrates a preferred embodiment illustrated in FIG. 1, when seen in the direction B—B.

According to FIG. 1, 2 or 3, the cathode 1 is conveyed to an inspection station and supported by support means 2 during the inspection of the surface of the deposit 11 located on the cathode. For the inspection, beams 4 of light are directed to the surface of the cathode 1 from a light source 3. The light source 3 is installed outside the area formed by the normals 5 of the plane 12 that constitutes the cathode surface, so that the beams 4 that reach the surface of the cathode 1 form an angle of 45 degrees with the centre line 6 of the plane that constitutes the cathode surface. Shadows 7 that are created by the beams 4 and cast by possible irregularities located on the surface of the cathode 1 are monitored by a camera 8, which is connected to an image processing device 9 and to a microprocessor 10 connected thereto, in order to classify the deposit 11 located on the surface of the cathode 1 advantageously for further processing.

Moreover, FIG. 3 illustrates how the surfaces of the deposits 11 located on both sides of the mother plate of the cathode 1 can be inspected in one and the same inspection station by placing a light source 3 and a camera 8 on both sides of the cathode 1.

What is claimed is:

1. A method for inspecting surface quality of a deposit created on a surface of an electrode in electrolytic treatment of metals, comprising illuminating essentially all the surface of a cathode obtained from electrolytic treatment by at least one light source placed in an oblique position with respect to a plane that constitutes the cathode surface, making an image of the illuminated surface with at least one camera, transmitting said image to an image processing arrangement, and on the basis of said image, defining possible irregularities of the surface in order to classify the deposit located on the cathode for a next processing step.

2. A method according to claim 1, wherein the light source illuminating the cathode surface is placed at an angle of 0–90 degrees, when measured at the spot where the beams coming from the light source meet a central line of the plane that constitutes the cathode surface.

3. A method according to claim 2, wherein the angle is between 30 and 60 degrees.

4. A method according to claim 1, wherein the light source illuminating the surface of the cathode is installed, with respect to the plane constituting the cathode surface, so that the light source is located outside an area formed by normals of the plane that constitutes the surface of the cathode.

5. A method according to claim 1, wherein in order to make an image of the illuminated surface, the camera is installed in an essentially perpendicular position with respect to the plane that constitutes the surface of the cathode under inspection.

6. A method according to claim 1, wherein in order to make an image of the illuminated surface, the camera is installed essentially in the centre of the plane that constitutes the surface of the cathode under inspection.

7. A method according to claim 1, wherein in order to make several images of the illuminated surface, cameras are installed essentially on the centre line of the plane that constitutes the surface of the cathode under inspection.

8. A method according to claim 1, wherein in order to classify the cathode on the basis of an image made by the camera, in said image there are defined shadows cast by the irregularities located on the surface of said cathode.

9. A method according to claim 1, wherein the images obtained from the surfaces of separate cathodes are recorded in a microprocessor provided in connection with an image processing device.

10. A method according to claim 9, wherein history information recorded in the microprocessor is utilised in adjustment of the electrolytic process.

11. A method according to claim 1, wherein the employed light source is a halogen floodlight.

12. A method according to claim 1, wherein the employed light source is a fluorescent tube.

13. A method according to claim 1, wherein the employed light source is an incandescent lamp.

14. A method according to claim 1, wherein the employed camera is a photographic camera.

15. A method according to claim 1, wherein the employed camera is a video camera.

* * * * *